United States Patent [19]

Andelman

[11] Patent Number: 5,779,891
[45] Date of Patent: Jul. 14, 1998

[54] NON-FOULING FLOW THROUGH CAPACITOR SYSTEM

[76] Inventor: Marc D. Andelman, One Parkton Ave., Worcester, Mass. 01601

[21] Appl. No.: 834,259

[22] Filed: Apr. 15, 1997

Related U.S. Application Data

[62] Division of Ser. No. 541,880, Oct. 10, 1995, Pat. No. 5,620,597, which is a division of Ser. No. 439,310, May 11, 1995, Pat. No. 5,547,581, which is a division of Ser. No. 194,609, Feb. 10, 1994, Pat. No. 5,415,768, which is a continuation-in-part of Ser. No. 27,699, Mar. 8, 1993, Pat. No. 5,360,540, which is a division of Ser. No. 819,828, Jan. 13, 1992, Pat. No. 5,200,068, which is a continuation-in-part of Ser. No. 792,902, Nov. 15, 1991, Pat. No. 5,192,432, which is a continuation of Ser. No. 512,970, Apr. 23, 1990, abandoned.

[51] Int. Cl.⁶ ..................... B01D 15/08
[52] U.S. Cl. ............ 210/198.2; 210/243; 210/541; 204/600; 204/645; 204/647; 204/671
[58] Field of Search ................... 204/600, 645, 204/647, 671; 210/635, 656, 747, 198.2, 243, 541

[56] References Cited

U.S. PATENT DOCUMENTS

| | | | |
|---|---|---|---|
| 3,658,674 | 4/1972 | Benak | 204/180 |
| 5,192,432 | 3/1993 | Andelman | 210/198.2 |
| 5,196,115 | 3/1993 | Andelman | 210/198.2 |
| 5,200,068 | 4/1993 | Andelman | 210/198.2 |
| 5,360,540 | 11/1994 | Andelman | 210/198.2 |
| 5,384,685 | 1/1995 | Tong et al. | 361/503 |
| 5,415,768 | 5/1995 | Andelman | 210/198.2 |
| 5,425,858 | 6/1995 | Farmer | 204/149 |
| 5,538,611 | 7/1996 | Otowa | 204/550 |

FOREIGN PATENT DOCUMENTS

| | | | |
|---|---|---|---|
| 9426669 | 11/1994 | WIPO | 210/198.2 |

OTHER PUBLICATIONS

Ganzi, "Water Purification and Recycling Using the CDI Process", Environmental Progress vol. 11, No. 1, Feb. 1992, pp. 49–53.

Johnson, "Desalting by Means of Porous Carbon Electrodes," J. Electrochem. Soc: Electrochemical Technology. Mar. 1971, pp. 510–517.

Publication by Allen M. Johnson et al. "The Electrosorb Process for Desalting Water." Mar. 1970, The Office of Saline Water Research and Development Progress Report No. 516, U.S. Department of Interior PB 200 056 pp. i, ii, iii, and 1–30.

*Primary Examiner*—Ernest G. Therkorn
*Attorney, Agent, or Firm*—Richard P. Crowley

[57] ABSTRACT

A foul-resistant, flow-through capacitor, a system employing the capacitor and a method of separation is disclosed wherein the capacitor has at least one anode and cathode electrode pair. The electrodes are formed of high surface area, electrically conductive material and have an open, preferably straight, fluid flow-through path. Typically, the flow path is formed by a plurality of straight, parallel, spaced apart electrodes with the flow path not greater than one of the X-Y-Z distance components of the capacitor. The flow-through capacitor avoids fouling in use and may be employed with saturated waste or other streams.

35 Claims, 12 Drawing Sheets

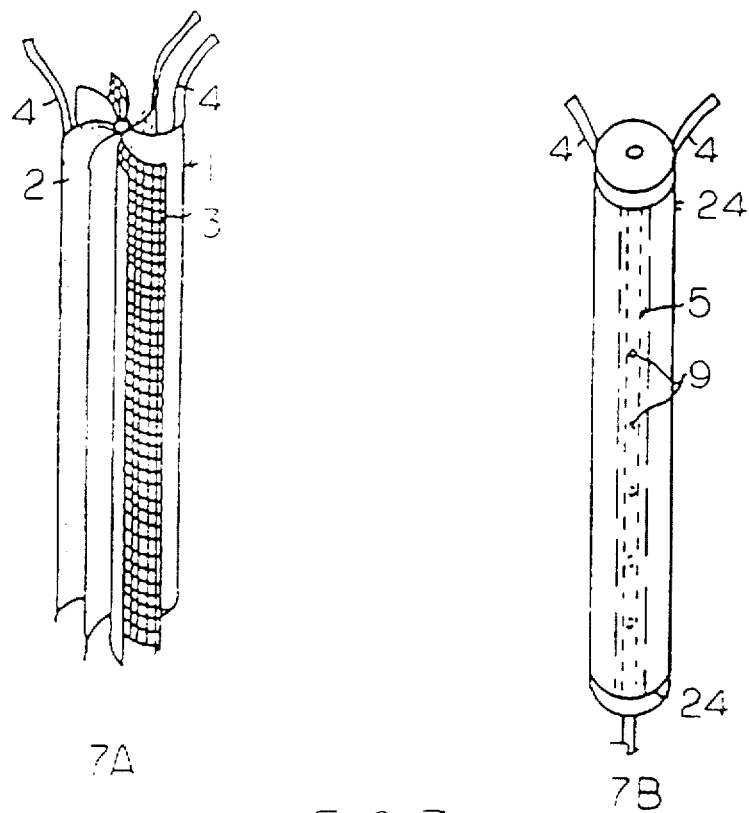
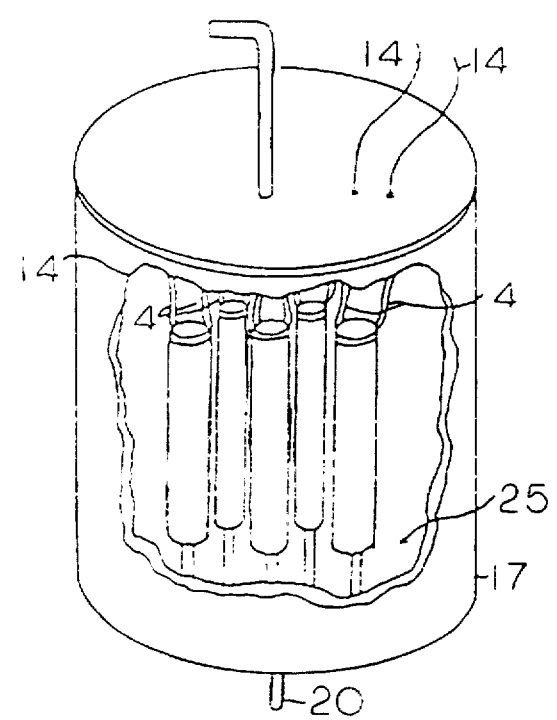
FIG. 7
FIG. 8

13A

13B

13C

13D

13E

13F

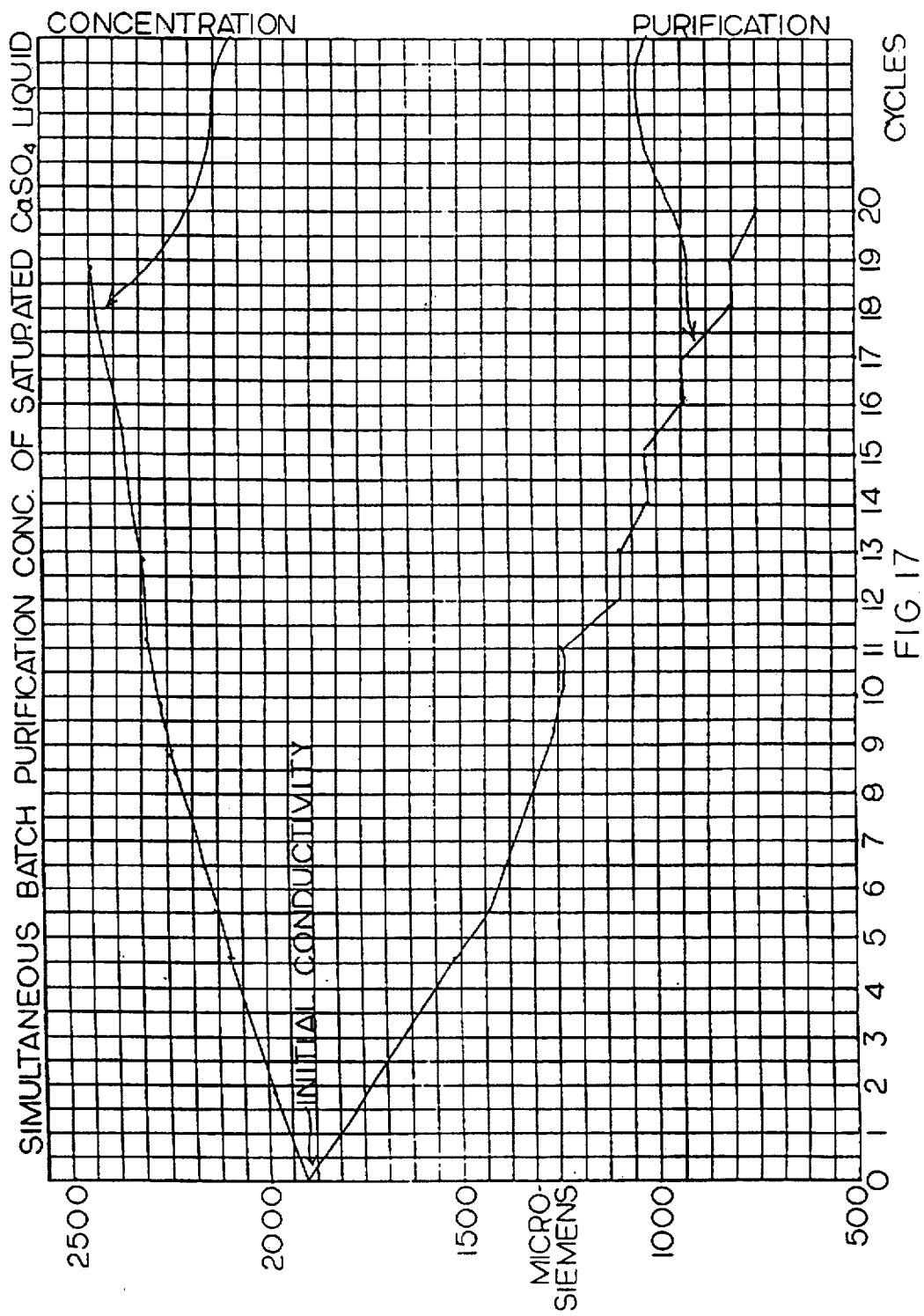

5,779,891

NON-FOULING FLOW THROUGH CAPACITOR SYSTEM

REFERENCE TO PRIOR APPLICATIONS

This application is a divisional application of U.S. patent application Ser. No. 08/541,880, filed Oct. 10, 1995, now U.S. Pat. No. 5,620,597, issued Apr. 15, 1997, which is a divisional application of U.S. patent application Ser. No. 08/439,310, filed May 11, 1995, now U.S. Patent No. 5,547,581, issued Aug. 20, 1996 which application is a divisional application of U.S. patent application Ser. No. 08/194,609, filed Feb. 10, 1994, now U.S. Pat. No. 5,415,768, issued May 16, 1995, which is a continuation-in-part of U.S. patent application Ser. No. 08/027,699, filed Mar. 8, 1993, now U.S. Pat. No. 5,360,540, issued Nov. 1, 1994, which is a divisional of U.S. patent application Ser. No. 07/819,828, filed Jan. 13 1992, now U.S. Pat. No. 5,200,068, issued Apr. 6, 1993, which is a continuation-in-part application of U.S. patent application Ser. No. 07/792,902, filed Nov. 15, 1991, now U.S. Pat. No. 5,192,432, issued Mar. 9, 1993, which is a continuation of U.S. patent application Ser. No. 07/512,970, filed Apr. 23, 1990, now abandoned. U.S. patent application Ser. No. 07/760,752, a divisional application of U.S. patent application Ser. No. 07/512,970, was filed on Sep. 16, 1991 and is now U.S. Pat. No. 5,196,115, issued Mar. 23, 1993. All of these patents and application are hereby incorporated by reference.

FIELD OF THE INVENTION

It has been discovered that a flow-through capacitor can be constructed with multiple, generally parallel open flow paths. The capacitor of the present invention utilizes this design and method to provide a fouling resistant flow-through capacitor with a compact and easy to manufacture construction.

BACKGROUND OF THE INVENTION

Flow-through capacitors have been described in the prior art (see for example U.S. Pat. Nos. 5,360,540, 5,192,432, 5,196,115, 5,200,068 and 5,415,768 to Andelman; U.S. Pat. No. 3,658,674 to Benak; and PCT International Application No. US94/05364 to Andelman. The publication by Allen M. Johnson et al "The Electrosorb Process for Desalting Water", March 1970, The Office of Saline Water Research and Development Progress Report No. 516, U.S. Department of Interior PB 200 056 and U.S. Pat. No. 5,425,858 to Joseph Farmer describe flow-through capacitors or flow-through deionization systems.

Flow-through capacitors of the prior art function by concentration of solutes in the feed stream into a concentrated waste stream. This has two serious disadvantages. The first disadvantage is that the method of waste recovery into a concentrated waste stream generates waste water. Waste water of any kind is often a significant process cost.

Another disadvantage of the prior art is tendency to foul. Solutes present in many ambient waters, such as Calcium Sulfate or Calcium Carbonate or other solutes, are present at or near saturation. When concentrated past the saturation point, such solutes have a tendency to form scales and foul the apparatus. Fouling is a well known problem in waste water apparatus, such as reverse osmosis and electrodialysis, that share with the flow-through capacitor the tendency to concentrate solutes past the saturation point.

Commonly present turbidity, colloids, and particles may also block flow channels and form deposits. Benak, U.S. Pat. No. 3,658,674, describes a flow-through capacitor that rapidly plugs up when used with hard well water (column 4 lines 66–68). He further describes (column 5, lines 27 through 37) problems with the purification of Calcium Sulfate. Prior art U.S. Pat. Nos. 5,360,540, 5,192,432, 5,196,115, 5,200,068 and 5,415,768 by Andelman, U.S. Pat. No. 3,658,674, the publication by Allen M Johnson et al "The Electrosorb Process for Desalting Water", March 1970, The Office of Saline Water Research and Development Progress Report No. 516, U.S. Department of Interior PB 200 056, and U.S. Pat. No. 3,658,674 by Benak all describe flow-through capacitors with a porous spacer layer. The pores in the spacer layer can be clogged up and fouled by turbidity already present in the feed stream, as well as by precipitates and crystals that form during use.

U.S. Pat. No. 5,425,858 by Joseph Farmer describes a flow-through capacitor whose spacer layers define an open channel with a long serpentine flow path. In the Farmer patent, the flow path is not also directly open to the outside, but is circumscribed by a gasket and forced to flow between holes in the successive multiple structural layers, and thence through an outlet. Serpentine channels provide bends where crystal and precipitates can settle, thereby blocking the flow path. Fluid flow-through holes in many successive structural layers further constrict the flow and offer many places for fouling to occur and multiple opportunity for solids to plug the flow path. A short flow path is preferable in order to flush the saturated waste out of the capacitor before the kinetic process of crystallization forms precipitates and causes fouling or crystals. The long flow path that a serpentine channel provides makes it difficult to flush the capacitor before crystallization occurs. Once solids do form inside the capacitor, it is that much more difficult to flush them through a long enclosed flow path.

The Farmer patent suffers from other disadvantages. The plate frame design depends upon multiple sealing gaskets. This provides multiple opportunities for leaks, and therefore requires hardware such as heavy, structural, metal end plates and threaded rods to tightly compress the stack. The structural, metallic end plates are conductive, and therefore, in addition to the gasket spacers, require an extra non-conductive insulator layer between the end electrodes and the end plate. The electrodes in the Farmer device consist of a titanium metal sheet sandwiched between two high surface area layers. To effect leak tight seals, the titanium metal sheets also have to be thick and structural, rather than the thin metal foils described in the Andelman patents. This adds to the cost and bulk of the system. Moreover, titanium is not the best choice, as titanium is a valve metal, and forms a non-conductive oxide coating under conditions which may occur during use of the flow-through capacitor. Finally, the Farmer device uses a conductive epoxy rather than a compression contact between the titanium sheets and the high surface area materials. This unnecessarily increases resistance of the electrical contact. The use of glue to form a contact would also shorten the lifetime of the capacitor device due to eventual deterioration of the bond.

There is therefore a significant and unfulfilled need for a new and improved flow-through capacitor apparatus, method and system. Such a capacitor would be resistant to fouling. It would furthermore be desirable that such a capacitor reduce or even eliminate the waste water entirely. Finally, it would be desirable for such a capacitor to be easy to manufacture, and not have any unnecessary parts that increase cost, or limit the usefulness of the capacitor.

SUMMARY OF THE INVENTION

The invention relates to a foul-resistant capacitor, system and method, and in particular, a capacitor, system and method for the separation of solutes or fluids which tend to clog or foul the capacitor.

The invention comprises a flow-through capacitor having at least one anode and at least one cathode adapted to be connected to a power supply, the capacitor arranged and constructed for use in the separation, electrical purification, concentration, recovery or electrochemical treatment or breakdown of solutes or fluids, particularly solutes and fluids which are saturated or substantially saturated and which tend to foul the capacitor.

The capacitor includes one or more spaced apart pairs of anode and cathode electrodes incorporating a high surface area electrically conductive material and characterized by an open, short solute or fluid flow path, which flow paths are in direct communication with the outside of the capacitor.

The fouling-resistant, flow-through capacitor of the invention is able to treat saturated solutions. The flow-through capacitor takes into account that subsequent formation of fouling precipitates and crystals from a super-saturated solution is a kinetic process. Therefore, the flow-through capacitor design is configured such that the fluid flow path through the capacitor is short, generally straight and open. To allow optimal and unobstructed wash out of solids in the capacitor, it is also desirable for this flow path to be open directly to the outside of the capacitor and not have to pass directly through multiple holes or constrictions. Therefore, the open channels created by the spaced apart electrodes communicate directly with the outside surface of the capacitor. These channels are not circumscribed by a gasket, but preferably have one dimension completely free of obstruction to flow. Where possible, it is also preferable to make the flow path wide.

A short, straight, open flow path, communicating directly with the outside surface of the capacitor has many advantages. A waste or feed solution, including a saturated or a super-saturated solution, can be flushed out of the capacitor before the process of crystallization takes place. Should the waste or feed solution be left in the capacitor long enough for crystals to form inside the capacitor, such fouling crystals can be flushed out through the straight and open flow path. Turbidity or particles present in the feed can also be flushed out through the capacitor without fouling the system. Because the flow path is directly open to the outside, it is also possible to clean mechanically between the electrodes without disassembling the capacitor.

The generally straight, short, open, wide flow path of the solute can be accomplished by replacing the porous spacer of the capacitors with multiple thin strips, shims, washers or open netting (such as sold by Nalle Plastics Inc. of Austin, Texas under the tradename Naltex), preferably including bidirectional filtration netting. Spacers may be any inert, non-conductive material, such as, but not limited to: fluorocarbon polymers, like Teflon®; ceramic beads; washer shapes; individual shims; or plastic netting, preferably biplanar filtration netting. The spacers may include microprotrusions screen printed onto the electrodes as disclosed in U.S. Pat. No. 5,384,685, "Screen printing of microprotrusions for use as a space separator in an electrical storage device", to Tong et al, hereby incorporated by reference. In short, any material in any shape which is thin in cross section and electrically non-conductive can be used to space apart the anode and cathode electrodes of the capacitor.

Spacers need not be separate layers, but may also be built into internal or external supports. For example, an internal supporting rod may contain risers or notches which are used to space apart the electrodes. The same thing may be accomplished with an external support or scaffold. To keep internal resistance of the capacitor as low as possible, the space between the electrodes should be as narrow as possible. Too narrow a flow path, however, increases the possibility of accidental shorting between the layers and enhances fouling. The optimal spacer thickness in one embodiment is less than about 50 mils, for example, between about 5 and 20 mils. Because the present invention does not require tightly sealed, gasketed spacers to form a flow path, the spacer material need not be elastic or rubbery in nature. The spacer material serves only to space the electrodes apart and not to form a seal in the capacitor. Therefore, only enough compression is required to hold the layers together, or to form an electrical contract between the conductive high surface area layers and any optional conductive backing layers to the electrodes. Either no end caps are required or less mechanically strong, non-conductive materials can be used, such as plastic materials. Therefore, the heavy structural metal end plates and connecting threaded rods can be eliminated. As a consequence, the insulator layer of the former or prior art devices disposed between the end plate and the end electrodes may be eliminated. There are many possible geometric configurations that combine a generally straight and open flow path. Preferably, the flow path should also be short, and directly communicate with the outside surface. Spacers may also and simultaneously function to provide internal support for a compression contract between high surface area layer conductive backing layers. Where possible, a wide flow path is also desirable. Generally, the present invention in the preferred embodiment employs multiple straight, parallel flow paths through the spaced apart electrode layers.

The width of the flow path should be short and, like the thickness, less than about 50 mils, and more typically, about 5 to 20–30 mils. The length of the flow path should also be short and should usually be the lesser dimension of the X-Y-Z dimensions of the capacitor, and for example, less than about 12 inches, for example, about six inches or less.

The electrodes may be made from any high surface area material. Where it is desirable to enhance the conductivity of the high surface area conductive material, a further conductive backing layer may be employed in direct contact with the electrodes. Where the intrinsic electrical conductivity of the electrodes is sufficient, this conductive backing layer may be eliminated. It is desirable to keep internal resistance in the capacitor as low as possible. Internal resistance sets a limit on charging time of the capacitor, which in turn directly limits the ultimate mass and fluid flow rates that it is possible to purify solutes and solutions. An internal resistance of less than about four ohms, e.g. one ohm, is preferred.

The electrodes may be made out of any monolithic high surface area conductive materials, in at least one anode/cathode pair. Where the high surface area material is conductive, but not optimally conductive, an electrical conductive backing may be employed. High surface area conductive materials suitable for use in the present invention include, but are not limited to: activated carbon; activated carbon treated with a halogen; carbon foams; carbon aerogel and aerogel composite materials; nanotubes; conductive polymers, especially in porous or network form; polymerized fullerenes; or any high surface area conductive material may be used. Conductive ceramics may also be used, either by themselves or impregnated onto high surface area substrates, including various forms of carbon such as fiber, foam, powder or aerogel. In general, absorbing any electrically actuated small or large molecule onto the conductive high surface area material that improves the capacitance will improve the function of the capacitor. Another preferred high surface area conductive material is conductive transition metal oxides, nitrides, or borides prepared using sol/gel technique. Powdered high surface area materials may be sintered into monolithic electrodes or bound together with binder materials.

Intrinsically conductive electrodes where no backing layer is required would include high surface area preparations of graphitic carbon, high surface area expanded metals, metal fibers, or metal meshes. For example, titanium fibers coated with high surface area platinum series black are known and are marketed as electrode materials. Other examples include platinum coated niobium and foamed metals. High surface area carbon materials may be mixed with metal or graphitic fibers or meshes and formed into monolithic units.

Another type of electrode includes a non conductive high surface area material in intimate contact with a conductive backing. An example of this would be an oxide layer on etched tantalum or aluminum, oxidized conductive ceramics, or thin films deposited on any high surface area conductive material. A capacitor with this material has the advantage that the solution is protected from direct contact with a conductive material. Therefore, the capacitor can be operated under much higher voltages, up to 50 volts or more, as opposed to a naked high surface area conductive material, which is limited by the breakdown voltage of the solution.

The invention will be described for the purposes of illustration only in connection with the embodiments; however, a person skilled in the art may make various modifications, changes, improvements and additions to the embodiments or illustrated embodiments, all without departing from the spirit and scope of the invention.

BRIEF DESCRIPTION OF THE DRAWINGS

FIG. 7A illustrates in partial assembled form a crescent-pleated capacitor;

FIG. 7B illustrates the assembled capacitor of FIG. 7A;

FIG. 8 shows a perspective, illustrative, partially cutaway view of a multiple manifold, flow-through capacitor of the invention;

FIG. 17 is a graphical representation of experimental data of electrical conductivity of a saturated $CaSO_4$ solution versus the number of charge and discharge cycles of the capacitor.

Different flow-through capacitor geometries can be employed that all share in common a short, straight and open, fluid flow path. All of such preferred designs in the drawings share in common multiple, parallel flow paths within the same capacitor, which for simplicity, is referred to in the singular in the below discussion. All of the capacitors also have in common a flow path that is in direct communication with the outside. FIGS. 1 and 2 show capacitors with washer style electrodes about a central tube or rod. The flow path is between the washer electrodes and out through the central tube. FIG. 6 shows a short, fat spiral wound arrangement, where the flow path is between the electrodes in the longitudinal direction, parallel the central axis. The spiral wound capacitor may contain a structural central rod or tube. The electrodes may also be fashioned as interlocking or overlapping pleats in various flat or cylindrical geometries. FIGS. 7A and 7B show a crescent pleat design where the electrodes are placed as overlapping pleats about a central tube, where the flow path is between the electrodes in the horizontal direction, and thence longitudinally out through the central tube, which contains holes along its length. Alternatively, it may be advantageous to replace the central tube with a fluted rod, such that the flow path is through ribs or channels along the length of the rod. FIG. 9 shows a flat capacitor made up of rectangular electrodes, with the flow path across the short dimension of the electrodes, between the electrodes. Alternatively, these multiple electrodes could be replaced by two or more interlocking pleated electrodes.

Figure 1:
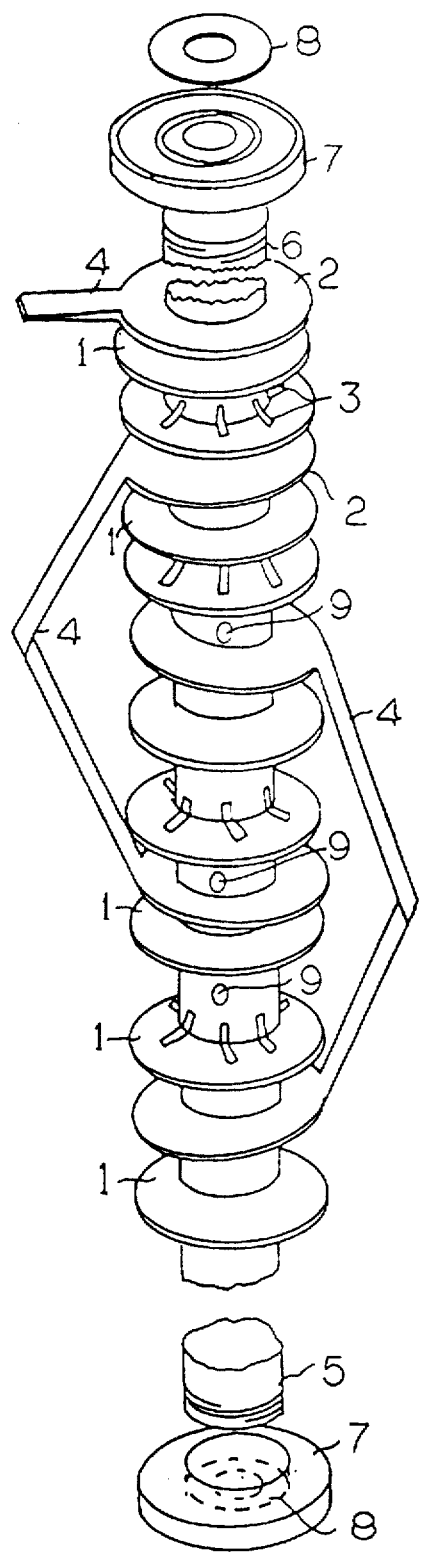
FIGS. 1 and 2 are schematic, exploded views of a washer-type capacitor of the invention.

In addition to shortening the flow path, the capacitor should be operated so that polarity is reversed in every charge cycle, so that no net buildup will occur on the electrodes. Since the electrodes are electrically active, reversing polarity makes the former anode into a cathode and the former cathode into an anode. Precipitates and deposits which may have favorably formed on one of either the anode or cathode will therefore be driven off, thereby further reducing fouling of the capacitor. To further minimize fouling, the flow-through capacitor should be backwashed by reversing the flow, for example, every charge or discharge cycle. This also helps avoid buildup of solids because there is no net flow in any one direction. It may also be desirable to continuously or occasionally operate the capacitor at slight overvoltage. This causes a small amount of electrolysis which keeps the electrodes clean of microbes and foulants.

The combination of a short, straight, open flow path, polarity reversal and optional backwash enables the flow-through capacitor of the invention to purify even saturated solutions, and to concentrate such solutions all the way until crystallization occurs. This phenomenon generates a further advantage. The fouling resistance offered by the straight, open flow path of the capacitor of the invention allows the flow-through capacitor to be operated to generate a solid instead of a liquid waste. To achieve this result, the flow-through capacitor is connected to a tank of saturated waste. During the regeneration cycle, the capacitor is filled with saturated solution from the waste tank. The capacitor is discharged into this saturated water, which is then flushed back into the waste tank. Precipitation occurs because, upon desorbing its ions, the capacitor super-saturates this saturated waste water. The straight and open flow path of the present design allows the precipitates to be flushed directly out of the capacitor for recovery or removal. The precipitate settles into the bottom of the waste tank, which can be collected separately by decanting or filtration. This process can be repeated indefinitely. The waste solution may alternatively, instead of forming a precipitate, become super-saturated. In this case, the solution can be triggered to precipitate by heating, cooling, vibration, seeding with small crystal, adjusting pH, or other precipitation methods.

A further disadvantage of prior art that is overcome by the present capacitor design is the dilution of product solution with dead volume of the capacitor. The capacitor described in U.S. Pat. No. 5,425,858 has a dead volume of 250 mls. This dead volume is deleterious, because waste solution left over after discharge needs to be flushed out with fresh feed solution, therefore generating additional waste water. If this waste solution is not adequately flushed out, then, upon charging the capacitor during a purification cycle, the capacitor repurifies in an inefficient manner the concentrated waste still present in the capacitor. This inefficiency gets worse with increasing feed solution concentration, due to the fact that the capacitor in this situation gets saturated faster, and needs to be regenerated more often. The more often the capacitor is regenerated, the greater the opportunity for contamination of product solution with the dead volume.

The flow-through capacitor of the present invention minimizes the dead volume problem, such as by connecting the capacitor to a source of pressurized gas, such as air, $N_2$ or other gases chosen not to react with or contaminate the product. The short and straight flow channels are optimal for allowing the solution inside to be displaced with a gas. In contrast, liquid contained in serpentine channels of a prior art capacitor would be more difficult to displace due to the tendency to form protected pockets. This displacement of dead volume with a gas or fluid is also difficult with the porous spacer design of the other patents, due to channeling. Any preference or unevenness in manufacture would cause channeling of gas or liquid fluids, and uneven displacement of the waste liquid with the gas. None of the prior art utilizes a gas to displace the dead volume.

Two or more foul-resistant, short flow path capacitors can be operated continuously in a system, one charging while the other discharges. To recover energy, a discharging capacitor can be used to charge other capacitors. Single charged capacitors can only be used to charge another capacitor until their voltages equalize. Among two capacitors of equal size, this wastes half of the energy in the discharging capacitor. However, two or more of these half charged capacitors can be connected in series. The series voltage of capacitors connected in series is additive. Connection of capacitors in series allows continued use of the depleted capacitors energy to charge other capacitors. U.S. Patent No. 5,475,858 describes the use of single capacitors for energy recovery to recharge other capacitors; however connection in series makes it possible to recoup energy from the remaining half of the unutilized energy.

Multiple capacitors in a system allow for alternating and continuous, simultaneous charge and discharge in order to provide uninterrupted product flow. Uninterrupted flow can also be achieved with a single flow-through capacitor by including a hold-up tank downstream that is used to average the flow between charge or discharge cycles. This allows for a simpler single capacitor system design.

A further improvement of the flow-through capacitor involves doping the carbon electrodes with a metal, such as platinum, titanium, or other metals with catalytic properties. This allows the capacitor to more easily electrochemically destroy chlorinated hydrocarbons, chloroform and other hazardous organic molecules. The metals overcome the activation energy of reactions such as removing a halogen from a hydrocarbon, or breaking down an organic molecule.

A preferred way to control the flow-through capacitor is to use the capacitor as its own sensor. In this system, both current and time are recorded, with the current measured through a shunt resistor. A computer integrates current versus time to calculate total charge that has been transferred into the capacitor. After a preset value of total charge has passed into the capacitor, a controller automatically activates the regeneration cycle, which involves first disconnecting the power supply, waiting a short time to safeguard the electronics, shorting the capacitor through a load, and actuating the appropriate valves and pumps that select and isolate the waste stream from the product stream.

DESCRIPTION OF THE EMBODIMENTS

FIG. 1 shows a stacked washer flow-through capacitor, whose high surface area electrodes contain a backing layer. The electrodes consist in combination of electrically conductive high surface area material 1 and conductive backing 2. The end electrodes may be either single or double sided, whereas the intermediate electrodes are preferably double sided. The electrical contact between the high surface area layer 1 and the conductive backing layer 2 is preferably a compression contact, which is afforded by the screw on end caps 7 tightened around central rod or tube 5 around threads 6. The electrodes are present in even numbers to form at least one anode/cathode pair. The anode and cathodes so formed are separated by spacers 3. Integral leads 4 extend from conductive backing (2).

These leads may be joined together to connect separately, in parallel alignment to themselves, the alternate anode and cathode layers, or they may be gathered together to accomplish the same purpose and to form an electrical lead.

Figure 4:
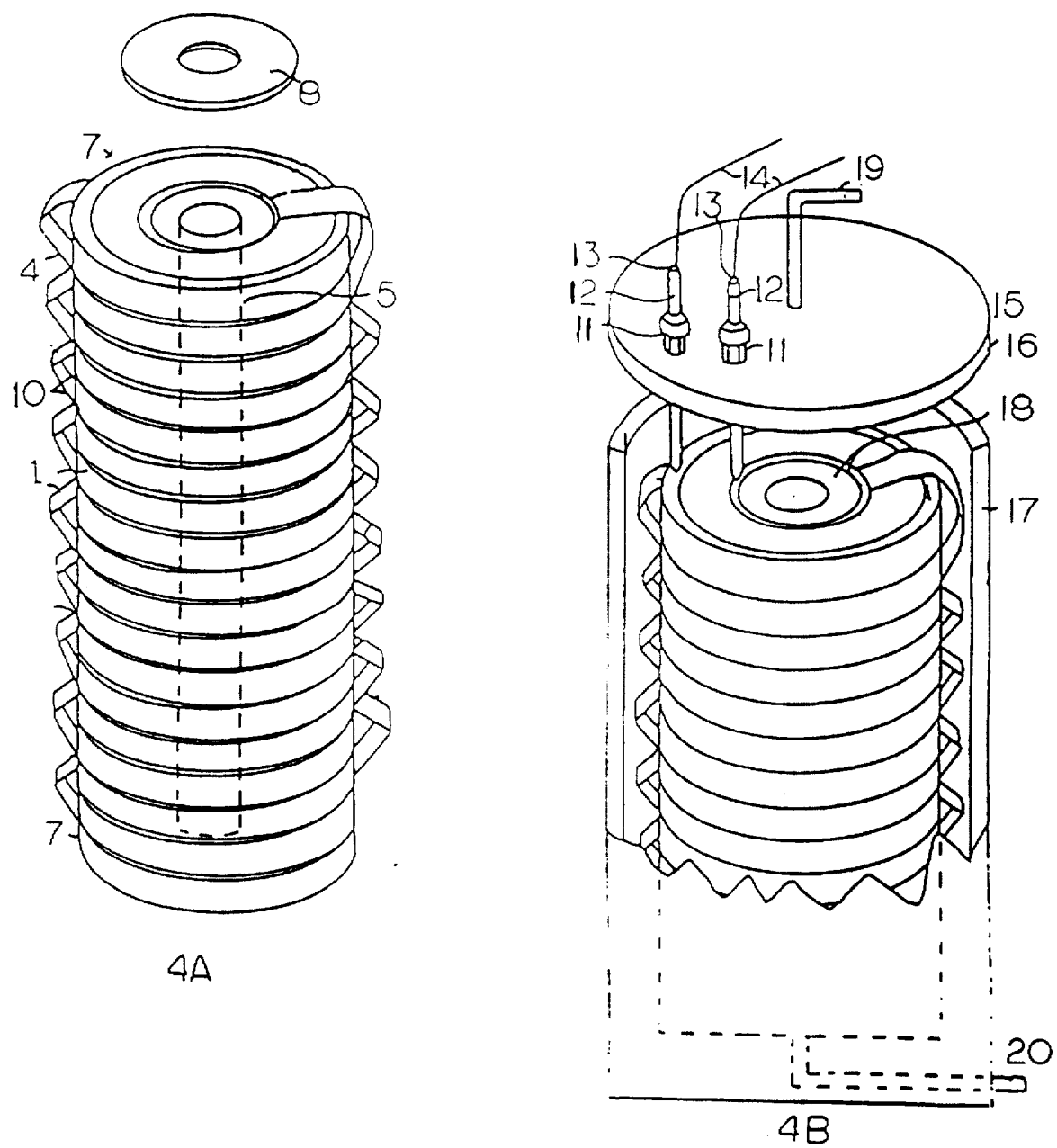
FIG. 4A shows an assembled capacitor cartridge of FIG. 1 or FIG. 2.
FIG. 4B shows the assembled capacitor cartridge of FIG. 4A within a cartridge holder with a partial cutaway view.

Fluid flow is between the spaced apart electrodes and through the holes 9 and then out through the central tube 5. Instead of a tube with holes, a ribbed rod may be substituted with fluid flow alongside the longitudinal ribs. Washer means 8 are provided to allow the cartridge to form a leak proof seal inside cartridge holders (see FIG. 4).

Figure 2:
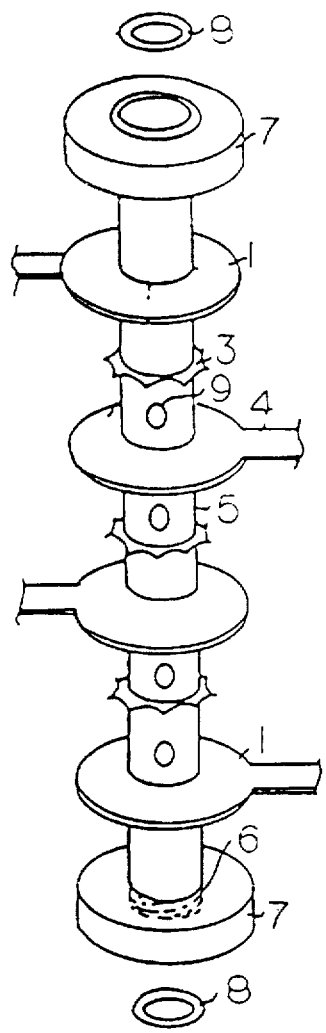

FIG. 2 shows a washer style flow-through capacitor with high surface area electrodes that are sufficiently conductive that no conductive backing is required. Integral leads 4 are attached to high surface area conductive material 1, which forms alternating anode cathode pairs separated by spacers 3.

Figure 3:
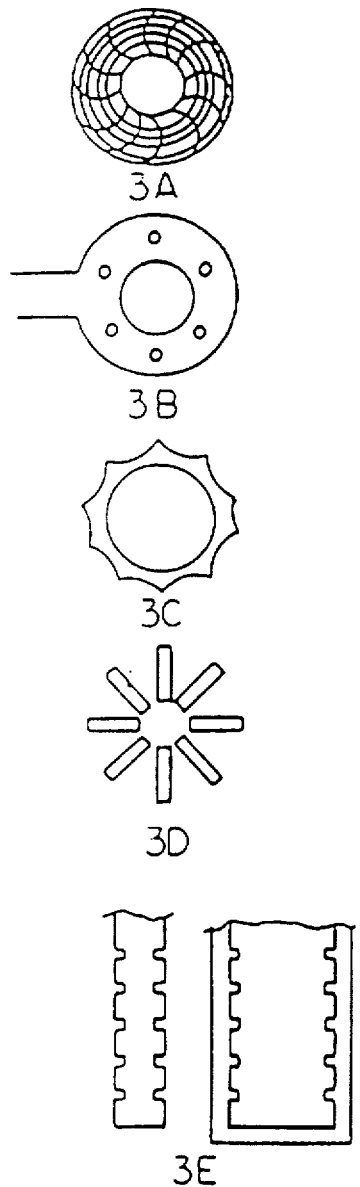
FIGS. 3A-G are representations of various spacers which may be used in the capacitor of the invention.
Figure 3:
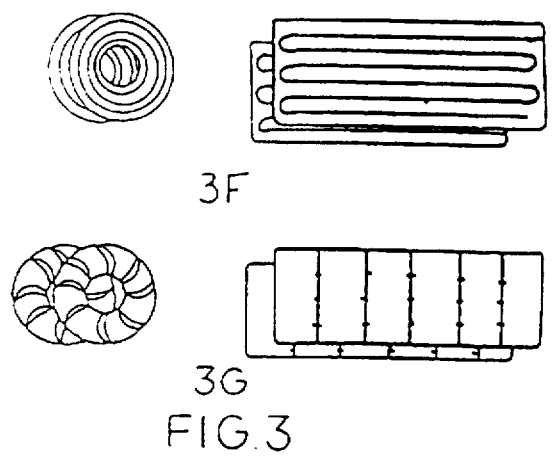

FIGS. 3A–G show various styles of spacers that may be used in the flow-through capacitor of the present invention. The spacer may be in the form of an open net (FIG. 3A), such as manufactured filtration netting (e.g. Naltex). This netting may be symmetrical or non-symmetrical. Biplanar netting is preferred, because this sort of weave does not obstruct the flow path along the surface of the netting. The spacer material may also consist of protrusions, such as the screen printed microprotrusions of U. S. Pat. No. 5,384,685 by Robert Tong et al. One preferred embodiment would be washer style circular spacers, such as the star-shaped spacer (FIG. 3C). Another preferred embodiment (FIG. 3D) would include individual shims, small rods, or threads, laid out between the anode/cathode layers to space these apart. Also depicted are spacers that are integrally formed from a central or external support, such as spaced notches in a central tube, or an external scaffold arrangement with spaced risers whereupon the electrodes are placed (FIG. 3E).

Under some circumstances, it may be desirable to deviate from a short straight flow path and provide instead for flow paths which are multiple, parallel, and generally open to the outside, but are also constricted; that is, long and serpentine. In this case, spacers as depicted in FIG. 3F and FIG. 3G may be used, as long as they are tightly sealed against the electrode surface. Constricting the flow to a spiral or serpentine flow path increases the linear velocity, which may have the advantage of providing greater turbulence and scouring action to remove foulants. This multiple flow serpentine flow path eliminates the likelihood of a severe pressure drop and provides a more effective technique over the prior art. While these spacers are shown to be used with the washer-style capacitor of FIGS. 1 and 2, it is recognized that they may adapted to be used with other capacitors.

It should also be noted that the multiple parallel flow paths allow the addition of extra length to the individual flow paths without a problem with pressure drop due to excessive elongation. Flow paths that are short and straight in the strictest sense are an ideal that is preferred in most cases. An exception would be, for example, a gel-like foulant such as iron hydroxide formation, which would require a turbulent or very fast flow to break up. The most common example requiring the shortest, straightest and widest flow path possible would be rapidly crystallizing solutions. In either case, the flow-through capacitor of the invention enables optimum function of the process due to the utilization of the shorter, multiple flow path design as desired.

FIGS. 4A-B show the assembled flow-through capacitor of FIGS. 1 or 2. The spacers create open space 10 between the high surface area conductive material 1. The washer shaped electrodes are assembled around central tube 5 and held in place by end caps 7. Leads 4 interconnect the alternate electrodes to form anode/cathode pairs. Anodes are connected to anodes and cathodes connected to cathodes, in parallel arrangement. FIG. 4B depicts the assembled flow-through capacitor of FIG. 4A in a cartridge holder 17. The cartridge holder is fitted with a lid 15 with threads 16. The lid contains two graphite rods 12. When lid 15 is screwed down upon cartridge holder 17, graphite rods come into electrical contract with the two concentric electrical contacts 18. These two contacts connect electrically to the bundled leads, which in turn interconnect the anodes and cathodes to themselves. The graphite rods 12 are attached to a spring 11 which provides a controlled tension and downward force that makes an electrical contact with concentric conductor 18. Metal caps 13 form a compression electrical contract with graphite rods 12 to connect electrically to wire leads 14, for connection to a DC power supply. The lid 15 is provided with an inlet 19, and the cartridge holder 17 is provided with an outlet 20. Washer means 8 seal against both the lid and the cartridge holder to form leak tight seals. The flow path is through the inlet, then between the spaced apart electrode layers, then out through the outlet.

Figure 5:
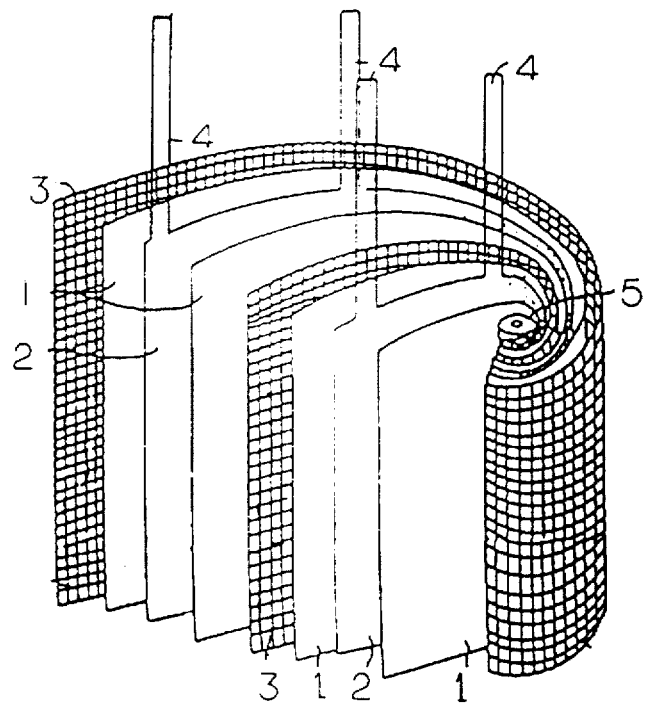
FIG. 5 illustrates in schematic view a short, fat, spiral wound capacitor of the invention in partial assembled form.

FIG. 5 depicts a spiral wound capacitor of the present invention utilizing conductive high surface area material 1, optional conductive backing 2, and spacer material 3 in a netting or open mesh form. Electric leads 4 extend from the electrodes formed from material 1 or the optional conductive backing 2. The capacitor may optionally be wound around a structural central rod 5. This capacitor is preferably made short and fat, with the width wider than the length of the capacitor as measured down the central axis.

Figure 6:
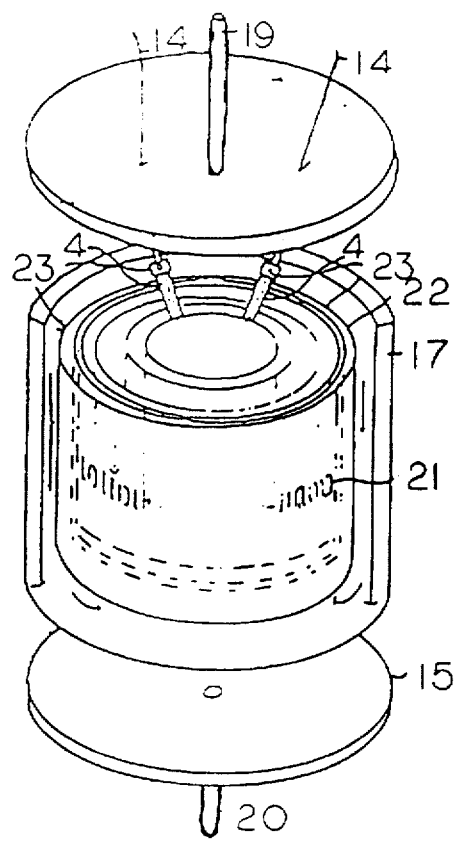
FIG. 6 illustrates the assembled, spiral wound capacitor of FIG. 5 within a cartridge.

FIG. 6 depicts the short, fat capacitor of FIG. 5 in a cartridge holder or piece of pipe 17. The pipe 17 is fitted with lids 15 containing inlet 19 and outlet 20. Integral leads 4 are bundled together in parallel. Wire leads 14 extend in a leak tight sealed manner through lid 15. A contact 23 is made between wire leads 14 and bundled leads 4. In cases where integral leads 4 are graphite foil, a compression contact is preferable, optimally using a gold or inert metal contact. The capacitor is sealed inside a shrink wrap plastic tube 22. In this embodiment, the central tube or conduit has one or more holes at a selected position in the tube, generally at the middle of the tube, and usually spaced apart about the periphery of the tube. Instead of sealing the capacitor layers themselves, the central tube is connected at both ends to outlet 20 (FIG. 6), or sealed at one end and connected at the other end to outlet 20 (FIG. 6). A gap is required in the surrounding spiral wound high surface area material layer (or layers) and optional conductive backing layer (or layers) by cutting slots or holes 21 (FIG. 6) therein, and aligning the cut holes or slots with the holes in the central tube to form a radial flow path. In this embodiment, fluid flow passes in the inlet 19, then moves both downwardly and upwardly between the electrode layers, through the space created by the spacer mesh or net spiral, until the fluid reaches the central gap or hole in the central tube, and the fluid is withdrawn from one or both ends of the central tube or conduit, then on through the outlet 20. Alternatively, a spiral wound capacitor can be tightly fitted inside a pipe or cartridge 17 with O-ring gaskets, in the same fashion as depicted with the bundled rod capacitor of FIG. 12. Here, the flow path is in through the inlet 19, down through the capacitor between the electrode layers, through the space created by the spacer mesh or net, and thence on through outlet 20. Lids 15 may also be in the form of end caps. Lids 15 and pipe 17 may be any material including metal, plastic, or ceramic, including PVC, Teflon, or stainless steel.

FIG. 7 depicts a crescent pleat design, where the individual layers do not complete a circuit around the center axis. The layers are made up of high surface area conductive material 1, optional conductive backing 2, and netting or open mesh material 3. Integral leads 4 lead directly off of material 1, or from conductive backing 2, where this optional conductive backing layer is employed. The layers are formed around central tube 5. Ends are sealed with any sealing means 24, including resins, such as urethane, epoxy, thermo-molded plastics, etc. The flow path is between the spaced-apart, conductive high surface area layers along the space created by spacers 3, through holes 9 and out through central tube 5. This flow path is not exactly straight, as it follows the curve of the crescent pleats along the shortest direction.

FIG. 8 depicts multiple capacitors of any style, such as for example the capacitors of FIG. 7, manifolded together with manifold plate 25 inside a single cartridge holder 17. Integral leads 4 are connected anode to anode and cathode to cathode by wires 14 with compression contacts 23. As shown in FIG. 6, wires 14 extend in a leak tight manner through lid 15 fitted with inlet 19. Flow path is through inlet 19, between spaced apart electrodes in the individual capacitors, then combined after flowing through manifold plate 25, thence out through outlet 20.

Figure 9:
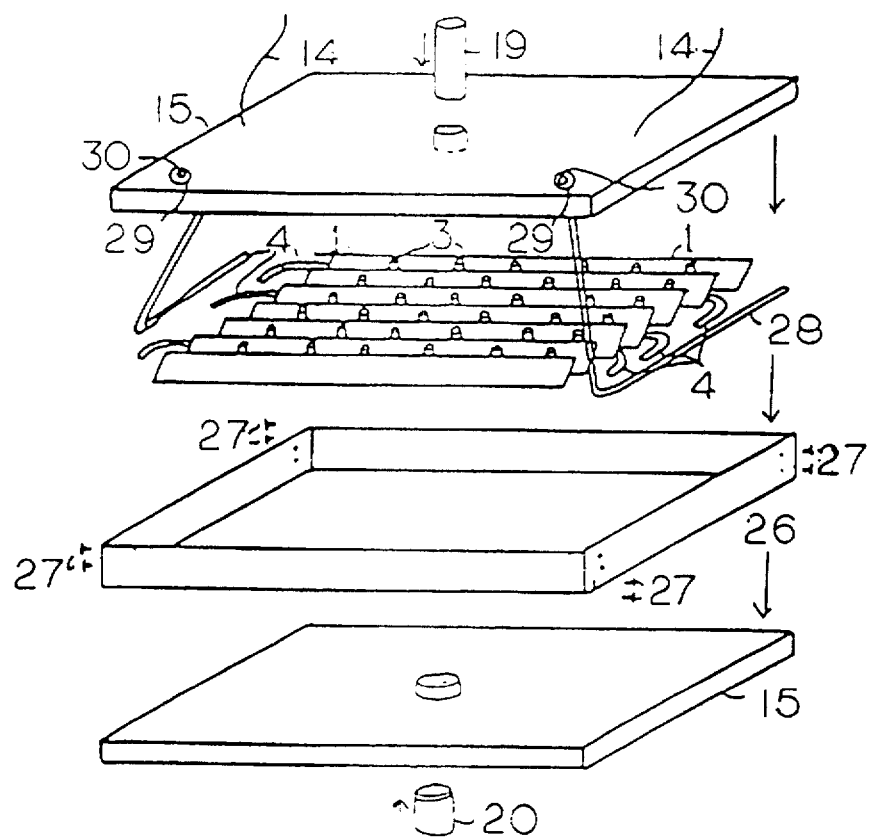
FIG. 9 illustrates in an exploded view a disassembled, flat-type capacitor of the invention.

FIG. 9 depicts a box-style flow-through capacitor. High surface area electrodes 1 are rectangular shaped, and are spaced apart by spacers 3. Spacers in FIG. 9 are depicted as shims, but may also be thin rods, threads, nets or open mesh, protrusions, or an outside scaffold. Integral leads extend from electrodes 1, and are bundled together in parallel, anode to anode and cathode to cathode, against electrode lead collectors 28. Electrode lead collectors are screw tightened against inside lid 15 and washers 29 with fasteners 30 to form an electrical connection with wire leads 14. The capacitor is placed snug inside box 26, which may be polygonal or circular in shape. Leak proof lids 15 with inlets 19 and outlets 20 are fitted onto box 26.

Figure 10:
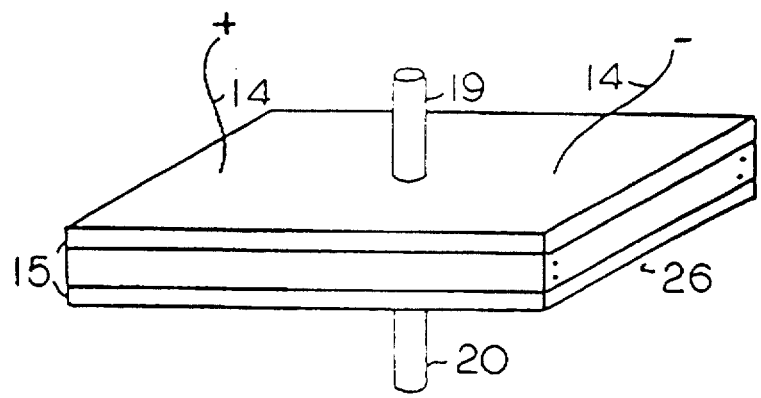
Fig.10 shows an assembled, flat, flow-through capacitor of the invention in a box-like cartridge.

FIG. 10 depicts the assembled flow-through capacitor of FIG. 9. The flow path is in through the inlet, between spaced apart high surface area layers 1. Optionally, the high surface area layers may sandwich a conductive backing.

Figure 11:
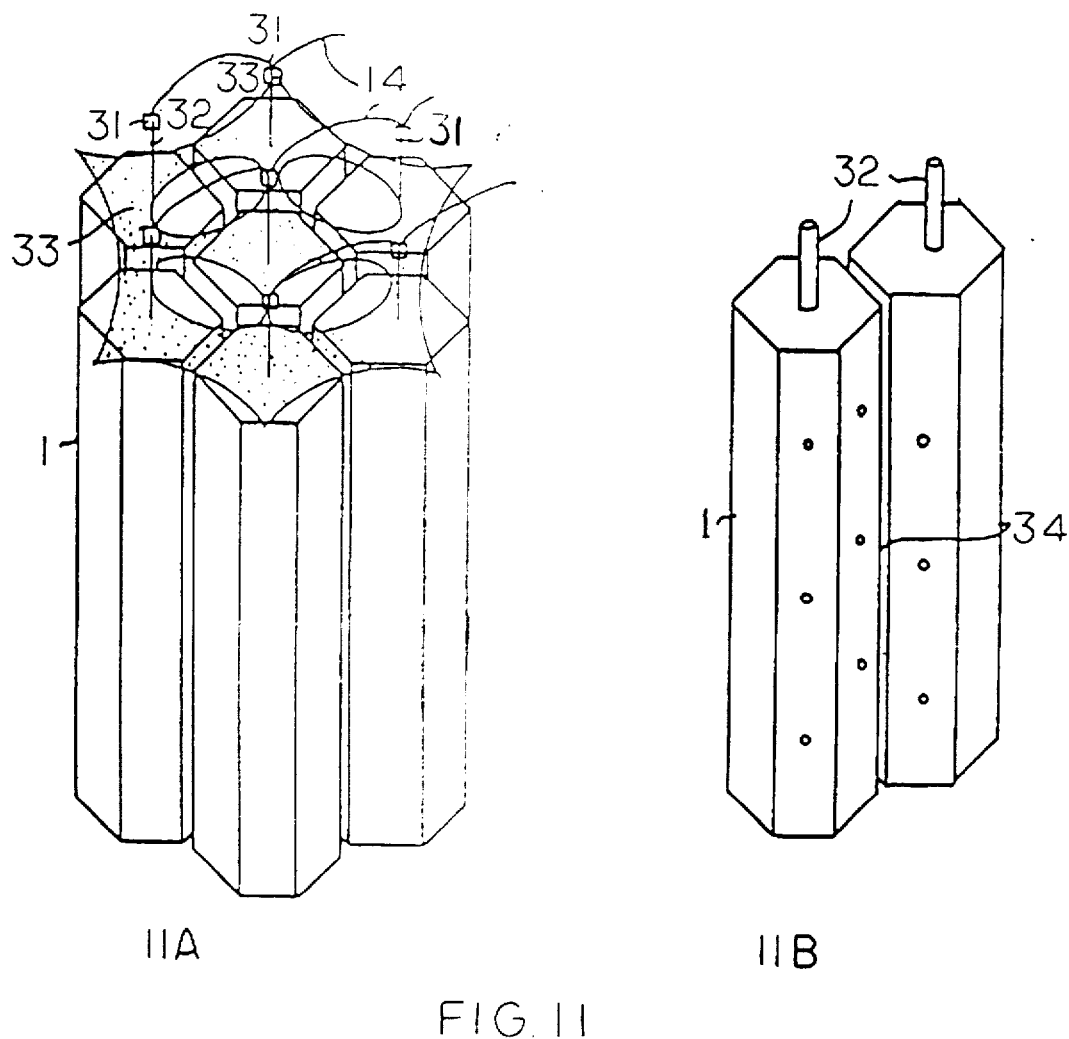
FIG. 11A is a schematic, perspective, partial view of a hexagonal rod capacitor of the invention.
FIG. 11B is a schematic, perspective, partial view of another embodiment of a hexagonal capacitor of the invention.

FIG. 11 depicts a rod-type electrode design. The conductive, high surface area material 1 is in the shape of circular or polygonal, e.g. hexagonal, rods. This conductive material may have a central conductive rod or tube 32, to form a conductive backing for the high surface area material. High surface area electrodes 1 are spaced apart by spacer scaffold 33 connecting central conductive rods 32. Alternatively, the high surface area electrodes 1 may be spaced apart by protrusions or shims 34. Wire leads 14 connect alternating electrodes anode to anode and cathode to cathode in parallel connection. This forms anode/cathode pairs exactly similar to flat electrode designs. Wire leads 14 are attached to central conductive rods 32 via metal cap connector 31. The metal cap connectors 31 are preferably an inert metal, such as gold or platinum, and form a compression fitting where the central conductive rods 32 are graphite. Central conductive rods may be any inert conductive material. Where the central conductive rods 32 are metallic, metal cap connectors 31 can be omitted and the rod may simply be drawn out or directly attached to wires 14.

Figure 12:
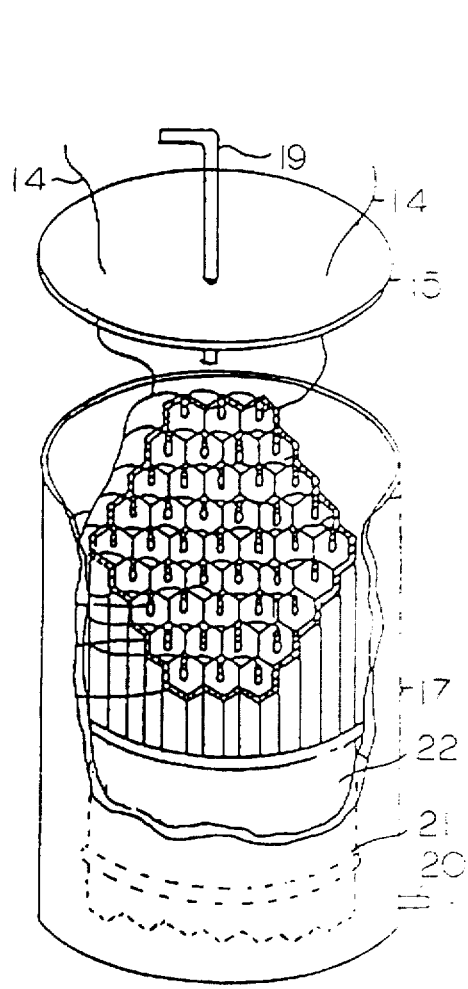
FIG. 12 is a schematic, perspective, partially exploded view of a hexagonal rod capacitor of FIGS. 11A or B in a cartridge.
Figure 13:
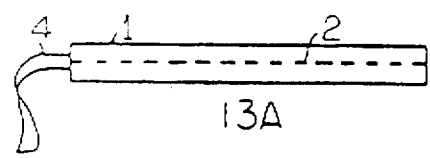
FIGS. 13A-F are schematic illustrations of various monolithic electrodes for use in the capacitor of the invention.
Figure 13:
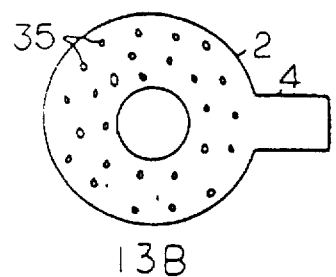
Figure 13:
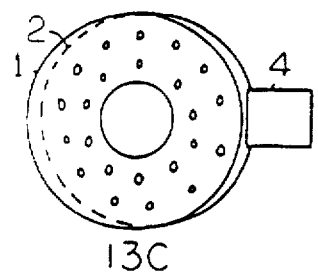
Figure 13:
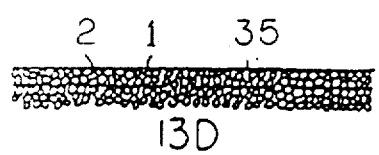
Figure 13:
Figure 13:
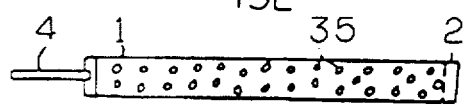

FIG. 12 is an illustration of an assembled rod-style capacitor with rods sealed together with shrink wrap plastic tube 22 and held against cartridge holder 17 with leak proof O-ring 21. Wire leads extend in leak tight fashion through lid 15, which seals against cartridge holder 17. Flow is through inlet 19, between spaced apart high surface area conductive polygonal electrodes, and out through outlet 20.

FIGS. 13A–F depict various monolithic electrode designs that incorporate an inner conductive backing. This is useful for all the above flow-through capacitors because a compression fitting is no longer required to make a contact between the high surface area layers and the conductive backing layers. The electrodes of FIG. 13 contain an inner conductive backing layer 2, which may be a metal foil, graphite foil, a fibrous material, or an interpenetrating network mesh material. In foil form, this backing material has many holes 35 therethrough to allow communication and interconnection with the high surface area material that forms a sandwich on both sides in a flat electrode. Alternatively, a rod style conductor can be used, with the high surface area material 1 formed directly around a central rod or wire conductor 32. This material is bonded together or calcined as a single, monolithic piece, containing the conductive backing internally. For example, activated carbon or aerogel powder may be mixed with a phenolic binder and hot pressed to form the shapes in FIG. 13, prior to calcining in the absence of air. The interconnections formed through the holes in the conductive backing hold the high surface area material together and prevent it from pulling away from the backing due to shrinkage during calcining. Alternatively, carbon films or layers may be deposited onto conductive backings, and activated in place. Integral leads 4 are formed from the internal conductive backing layer or rod 32.

Figure 14:
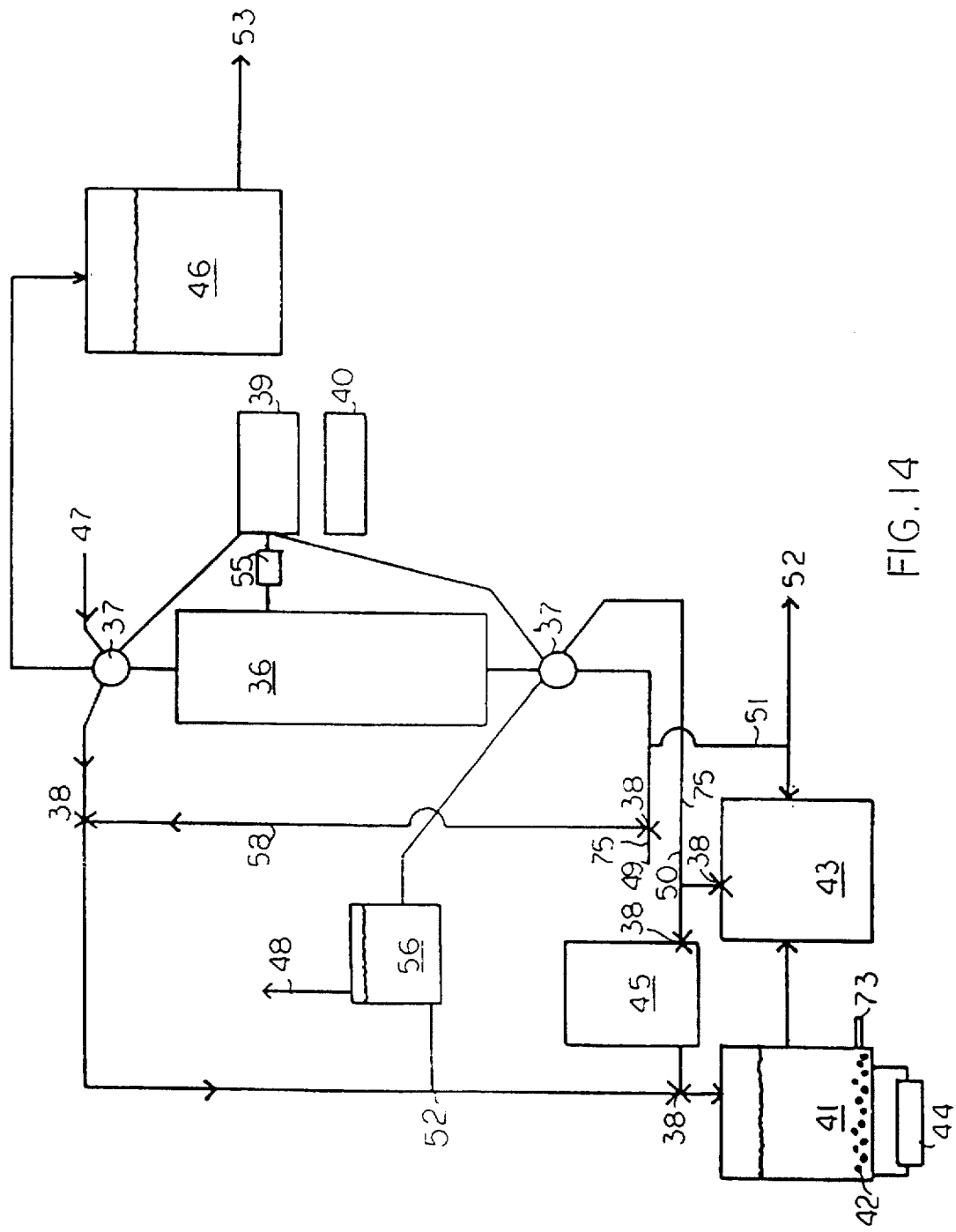
FIG. 14 is a schematic illustration of a system employing the capacitor of the invention.

FIG. 14 represents a diagram of a flow-through capacitor system. The flow-through capacitor 36 connected to manifold valves 37 and DC power supply 40 are controlled by computer or programmable logic 39. The feed solution 49 contains solution that is pumped or fed through capacitor 36 during the charge cycle to form purified product. Hold up tank 46 pools the product flow produced during the charge cycles to provide an averaged, continuous product flow 53. Counter 55 measures how much current versus time goes flows into the capacitor, preforms an integral of current versus time to calculate charge, and automatically starts the discharge cycle after a preprogrammed amount of charge has passed into the capacitor. This charge is a cutoff point that corresponds with a desired level of saturation of the capacitor.

Alternatively, the capacitor may also be controlled with sensors that monitor conductivity, pH, or concentration of feed, product, and waste solution. At this point, the power supply is first disconnected, and, after a short time interval for safety purposes, the capacitor is discharged through a load. During discharge of the capacitor, waste solution stored in tank 43 is shunted through three way valves 38 and manifold valves 37 and pumped through the capacitor in a loop back into settling tank 41. The ions absorbed during the charge cycle of the capacitor are desorbed and discharged into this waste solution during discharge of the capacitor. The waste stream 50 gradually becomes saturated or supersaturated. Settling tank 44 is fitted with a heat exchanger 44 which functions to change the temperature of supersaturated wastes in order to provoke crystallization from solution.

Crystals 42 that flow into or form in the tank 41 settle to the bottom, where they may be recovered through outlet 73. The saturated waste is decanted into tank 43, for use in the next discharge cycle. Saturated waste may be bled off directly through outlet 52. This may be replaced with make up solution through make up loop 51, which cross connects with feed stream 49. After discharge of the capacitor, saturated waste is returned to the tanks 41 and 43. Manifold valves 37 then actuate to close off the capacitor to both the waste and the feed streams, and open it up to a compressed gas stream 47.

This gas stream displaces the waste solution from the capacitor, where it is driven into gas separation tank 56. Saturated waste liquid from tank 56 is recombined with the saturated waste stream through three way valve 57. Gas is exported from tank through outlet 48. It may also be desirable to likewise displace the feed solution with compressed gas after a charge cycle. Compressed gas stream 47 may be replaced with steam, which reactivates activated carbon electrodes and sterilizes the capacitor from microorganisms. Shunting loop 58 allows the direction of the feed solution through the capacitor to be reversed on alternate charge cycles in order to backwash the capacitor. This further prevents net build up of turbidity and foulant. All liquid solutions should first be fed into the bottom of the capacitor in order to displace all of the air, after which the flow may be maintained in this direction or reversed via shunting loop 58 to provide a backwash cycle.

Finally, reconditioning tank 45 contains reconditioning solutions that are used to remove such absorbed materials, such as metals which electroplate onto the electrodes, organic foulants, or microbiological contaminants. It may also be important to adjust the pH of the feed solution, especially when dealing with easily plated metals. The object is to adjust the pH or add other ingredients to the feed solution in order to keep the plating voltage as high as possible. This allows the capacitor to operate more effectively via its capacitance mode and electrostatic absorption rather than by electrowinning and electroplating of metals onto the electrodes. Electroplated metals require acids, bases, oxidizers, solvents, or other additional chemicals to recondition the electrodes and recover the plated metals, via reconditioning tank 45. As desired, a pump 75 may be included along feed streams, such as feed stream 49; waste streams, such as waste stream 50; or any other streams.

Figure 15:
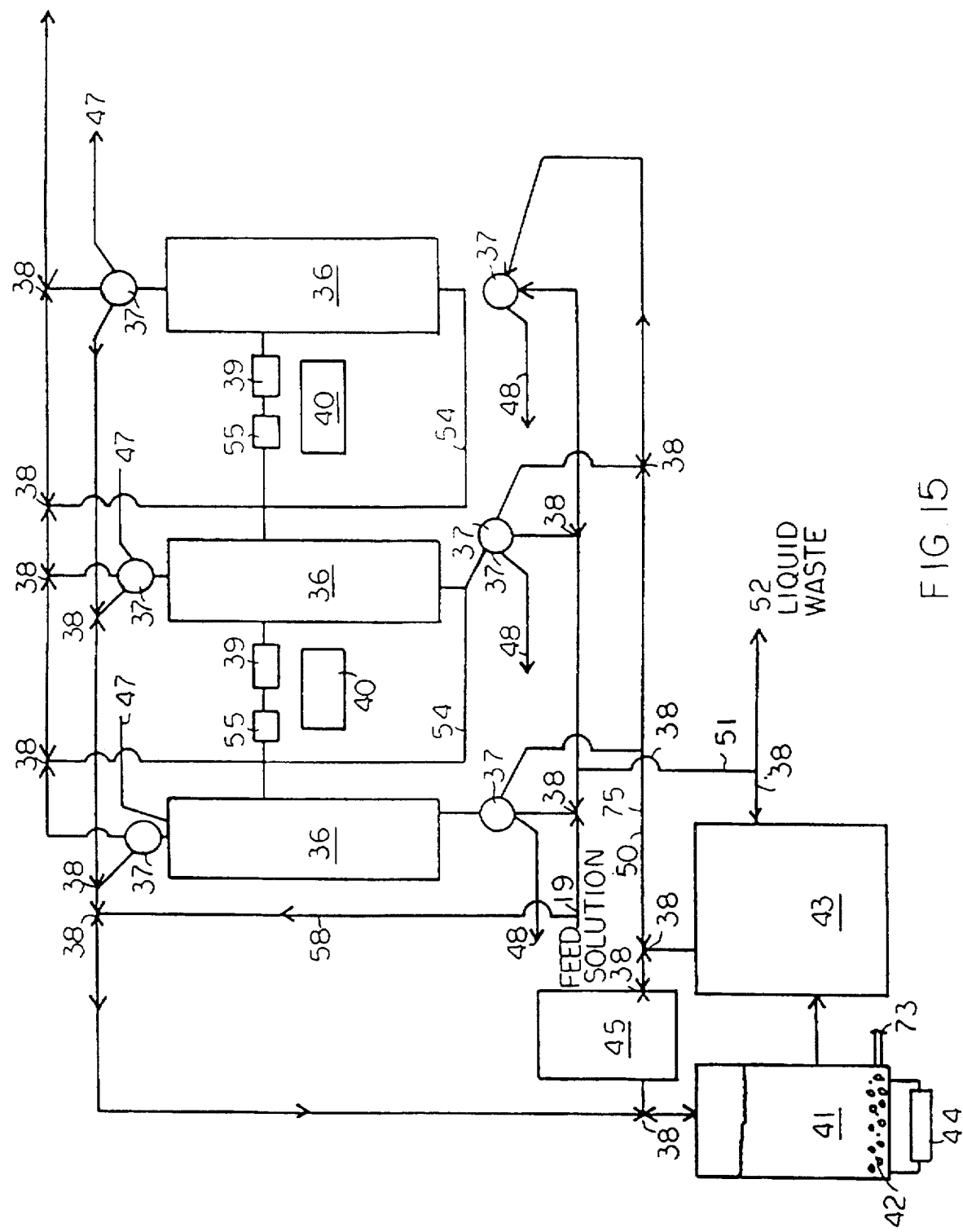
FIG. 15 is a schematic illustration of a multiple capacitor system of the invention.

FIG. 15 shows a multiple capacitor system, with continuously charging and discharging capacitors to achieve continues product flow, as opposed to the single capacitor and flow averaging tank of FIG. 14. The flow path of capacitors 36 may either be connected in parallel, or may alternatively be connected in series through shunt 54. Series connection of the flow path allows successive staged purification of a concentrated solution to very high purity product solution 53. Other components function and are as numbered in FIG. 14.

In another embodiment, it may be desirable to provide baffles in one or more or all of the flow passages to create a flow turbulence to the fluid through the flow passages to scour the surfaces to discharge foulants or to remove foulants from the flow passages. The value of the use of baffles for flow turbulence should be balanced with any pressure drop which results from the use of such baffles.

In order to create turbulence, baffles can be formed between the electrode layers, either constitutively with the electrode material or more easily with the spacer material. Increasing the flow rate of the capacitor may also be desired. The baffles create turbulence, which scours foulants from the electrode surface.

Other methods to prevent and treat fouling include washing the capacitor with purified product solution. This can be accomplished simply by reversing a pump 75 placed along the feed or product stream, and pumping purified solution back from hold up tank 46 depicted in FIG. 14. Alternatively, an extra shunting loop may be added.

Organic foulants tend to accumulate on the electrode surface. Microorganisms tend to grow and multiply on the electrodes, especially activated carbon. Temporarily running the capacitor at a high enough voltage to cause the electrolysis will actively clean the electrodes. Also, continuously running the capacitor at a slight over-voltage to cause continuously a little electrolysis will also keep the electrodes clean.

The capacitor may be part of a train that includes other water purification technologies, including electrowinning, ion exchange, RO, ED, microfiltration and ultrafiltration, either upstream or downstream in the capacitor. For example, it may be desirable to add microfilters as a prefilter to remove fouling causing turbidity, or as a postfilter to remove carbon fines. A granular activated carbon prefilter may be desirable to further protect the capacitor from organic foulants. Greensand or oxidation means may be employed upstream of the capacitor to remove iron, which forms a slimy hydroxide that would tend to foul the capacitor. To produce ultrapure water, it may also be desirable to include a deionization ion exchange bed downstream of the capacitor as a final polishing step.

EXAMPLE 1

A stacked washer flow-through capacitor of FIG. 2 was assembled using sintered activated carbon for the high surface area layer (1) and 5 mil thick graphite foil from Polycarbon for the conductive backing (2). The sintered activated carbon washers were obtained from Kansai Coke and Chemicals, Ltd. These washers had an outside diameter of 1.5 inches and an inside diameter of 0.75 inches. They were 0.046 inches thick. The specific density was 0.7 grams/ml, and the ratio of activated carbon to binder was 7:3. The activated carbon used had a BET surface area of 2000 square meters per gram. The central tube was 1 inch long, $\frac{3}{8}$ inch OD, and ¼ inch ID PVC, with holes drilled in the side with end threads (6). End caps were 0.25 inch thick PVC, 1.8 inch diameter, with internal threads that allow the end caps (7) to screw onto both ends of the central tube (5). Spacers consisted of six Teflon shims 0.75 inches long, $\frac{1}{16}$ inch wide, and 0.01 inches thick. These were laid out radially on top of the electrodes, as depicted on FIG. 3D. The anode and cathode electrodes where formed of ten sintered carbon washers of ten grams total which formed four intermediate double-sided electrodes, with the sintered activated carbon conductive high surface area material (1) sandwiching the conductive backing (2), and two single sided end electrodes with the conductive backing on the outside, between the sintered activated carbon conductive high surface area material (1) and the end caps (7). Tabs (4), formed integral to the conductive backing layers (2), were gathered up to form anode and cathode leads, which were connected via a gold compression contact to wire leads which led to a DC power supply.

This capacitor was not placed inside a cartridge holder. One end of the central tube was sealed with urethane resin. The other end was connected to a length of plastic tubing, which in turn led to a pump. The flow-through capacitor was placed inside an open 200 ml container of feed solution, which was pumped through the capacitor under negative pressure. Alternatively, the tubing end could be placed in the feed solution, and solution could be pumped through under positive pressure.

Figure 16:
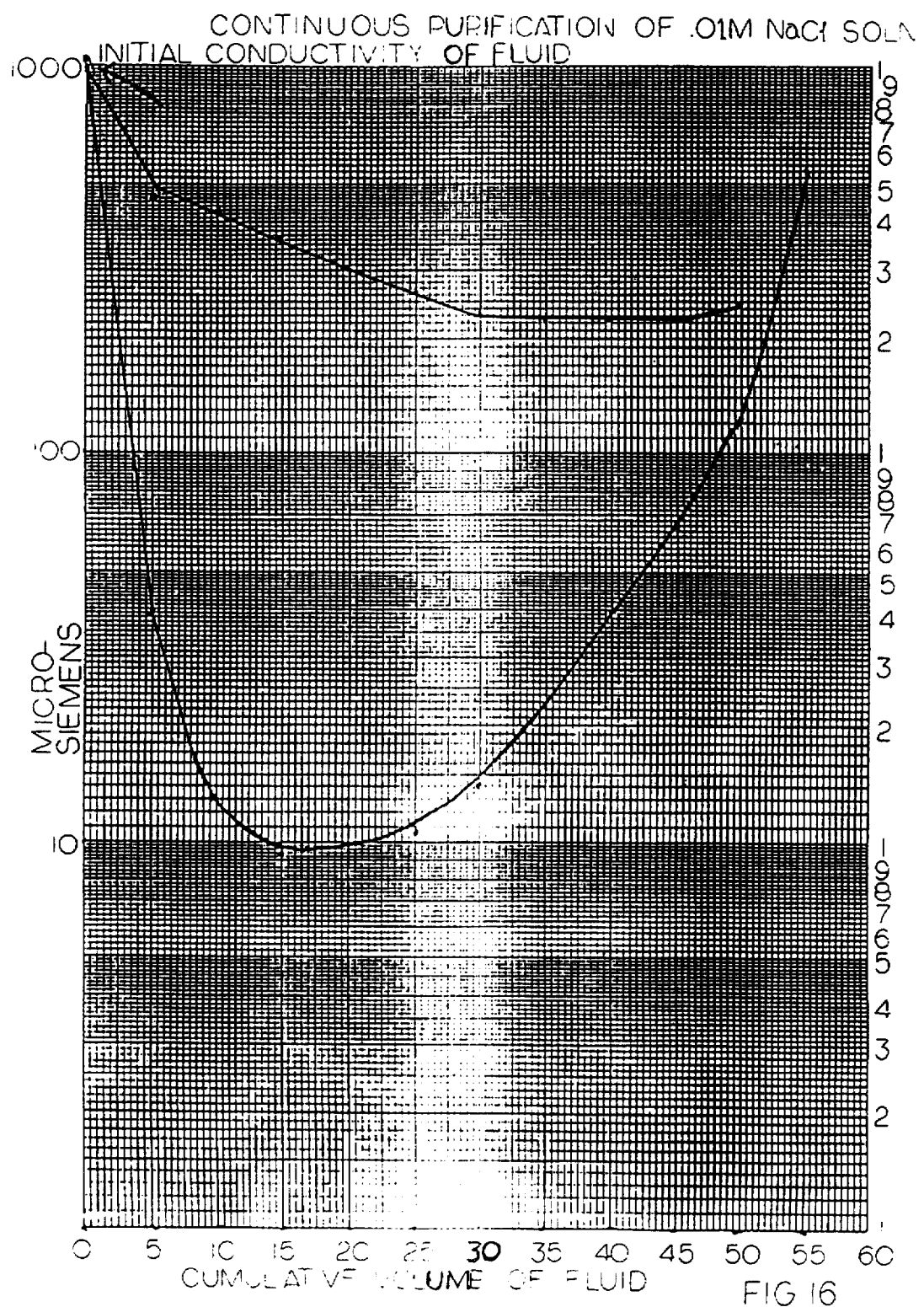
FIG. 16 is a graphical representation of experimental data of electrical conductivity of a NaCl solution in microSiemens versus cumulative volume of fluid in ml.

FIG. 16 graphically illustrates Experiments 1 and 2 with non-saturated NaCl feed to demonstrate the utility of the present invention. These experiments used the flow-through capacitor described above in Example 1.

Experiment 1 —Continuous Purification of NaCl
Conditions:
 Feed solution 1035 micro Siemens NaCl
 Flow rate 0.58 ml/minute
 Voltage—2 volts
Results:
This experiment demonstrates more than a two order of magnitude purification starting from 1035 micro Siemens feed to 9 micro Siemens product. This demonstrates that a very pure product stream can be produced starting with a concentrated feed solution. This further demonstrates that a capacitor designed with many short parallel flow paths, as opposed to long serpentine flow paths, produces very high purity product.

Experiment 2—Continuous Purification of NaCl at Fast Flow Rate
Conditions:
 Feed Solution 1035 micro Siemens NaCl
 Flow rate 4.2 ml/minute
 Voltage 2 volts.
Product solution—to as low as 223 micro Siemens This experiment demonstrates a greater than 75% purification with a flow rate that is more than seven times faster than Experiment 1.

FIG. 17 graphically illustrates Experiment 3 which tests the utility of the present invention with a saturated feed stream. The capacitor used in Experiment 3 is as described in Example 1 above.

Experiment 3—Simultaneous Batch Purification and Batch Concentration of Saturated $CaSO_4$.

Saturated $CaSO_4$ is made by mixing distilled water with an excess of $CaSO_4$ and letting the mixture sit on the excess solids overnight.

Initial Conditions:

Initial conductivity of saturated $CaSO_4$ solution is 1906 micro Siemens. This saturated solution is divided into two equal 200 ml volumes.

Flow rate: 12.5 ml/minute, batch flow. Batch flow means that fluid is pumped in a circular loop through the capacitor and recombined with the feed solution.

Procedure

A capacitor is connected to one of the two 200 ml saturated $CaSO_4$ solutions and run in batch mode at 2 volts for five minutes. Air is then pumped through the capacitor until capacitor is completely drained. Solution from the second 200 ml volume of saturated $CaSO_4$ is then pumped through the capacitor while simultaneously short circuiting the capacitor. This process is repeated twenty times, always reusing the same solutions for the purification cycle and concentration cycle. Polarity was reversed between every charge cycle.

A graph of the results is depicted on FIG. 17. After twenty charge cycles, the batch purified solution is purified down to 802 micro Siemens. After twenty discharge cycles, the batch concentrated solution is concentrated up to 2470 micro Siemens. This concentrated solution has become super saturated. Upon raising the temperature of this super saturated solution in a hot water bath, crystals were observed to drop out of solution. Decanting this solution provides a saturated solution which can be saved and reused as a regeneration stream. The separated crystals may be collected as a solid waste.

An interesting phenomenon is observed when purifying saturated solutions. After about 10 charge/discharge cycles, the capacitor is observed to purify the batch purification solution in a step wise manner. This is shown on the graph of FIG. 17. Purification of the batch 200 ml solution begins to chiefly occur every other charge cycle. Precipitates that form from the saturated solution form more favorably on one of either the anode or the cathode and must first be desorbed before any new net absorption can occur in the purifying solution. This causes a step wise behavior that is observed in FIG. 17.

What is claimed is:

1. A flow-through capacitor-cartridge system for use in the electrical treatment of fluids which tend to foul the capacitor of the system, which system comprises:

a) one or more foul-resistant, flow-through capacitors, each capacitor having at least one anode and cathode pair for use in the electrical purification, concentration, separation, recovery, or electrochemical breakdown of solutes or fluids, which capacitor comprises one or more monolithic, spaced apart pairs of cathode-anode electrodes incorporating a high surface area material and having a non-conductive spacer between the anode and cathode electrodes characterized by an open flow path between the electrodes to permit the unobstructed flow of the fluid across the electrode surface and of sufficient width to prevent the fouling of the capacitor, and wherein the open flow path has at least one dimension open to an exterior of the capacitor; and b) cartridge means to seal the capacitor therein, the cartridge means having a fluid flow feed inlet and a fluid flow product outlet.

2. The system of claim 1 wherein the cartridge means has a liquid dead volume and which system includes means to displace liquid from the dead volume by pressurized gas.

3. The system of claim 1 which includes a feed source of saturated waste in communication with the feed inlet and for processing by the capacitor and means to recycle the saturated waste and to recover from the product outlet the waste as a solid precipitate.

4. The system of claim 3 which includes a decantation tank, provided with means to trigger precipitation from a super-saturated solution.

5. The system of claim 1 which includes a control means to control the system by integrating current versus time to calculate a set amount of charge which triggers a regeneration cycle of the capacitor.

6. The system of claim 1 which includes a single capacitor and a hold-up tank to average the flow of the fluid being processed through the cartridge means to provide a continuous product stream.

7. The system of claim 1 which includes three or more simultaneously regenerating capacitors in the system and wherein multiple capacitors are electrically connected in series and used to recharge a lesser number of capacitors in the system.

8. The system of claim 1 wherein the flow of the fluid into the flow inlet through the capacitor is reversed every charge or discharge cycle or wherein polarity of the electrodes is reversed every charge or discharge cycle.

9. The system of claim 1 wherein the open flow path is relatively short and is no longer in length than the length or height of the electrode.

10. The system of claim 1 wherein the open flow path is straight.

11. The system of claim 1 wherein the flow path comprises multiple parallel flow paths.

12. The system of claim 1 wherein the flow path comprises multiple serpentine flow paths.

13. The system of claim 1 wherein the flow passages include baffle means within the flow path of the fluid to create flow turbulence for cleaning purposes.

14. The system of claim 1 wherein the open flow paths comprise a plurality of generally parallel, straight flow paths comprising at least as many flow paths as there are spaces between the electrodes.

15. The system of claim 1 wherein the width of the flow path is less than about 50 mils.

16. The system of claim 1 wherein the space between the electrodes forms an open flow path following the contours of the electrodes along the shortest, straightest route to the exterior surface of the capacitor.

17. The system of claim 1 wherein the spacer material comprises integral pieces of material in washer or netting form.

18. The system of claim 1 wherein the spacer material comprises multiple shims, protrusions, rods or threads.

19. The system of claim 1 wherein the spacer material is manufactured directly attached to the high surface area electrode material in the form of ridges, multiple individual protrusions or ribs.

20. The system of claim 1 wherein the monolithic high surface area material is selected from the group consisting of: bonded or sintered activated carbon particles; aerogel particles; conductive ceramics; activated carbon fiber cloth; fibrous metal coated with platinum; or transition metal oxides, borides and nitrides, and combinations thereof.

21. The system of claim 1 wherein the monolithic high surface area material comprises activated carbon sintered together with a binder and doped with a metal.

22. The system of claim 1 which includes a conductive backing electrically secured to the high surface area material.

23. The system of claim 1 wherein the conductive backing comprises integral metal or graphite foil sheet material.

24. The system of claim 1 wherein the capacitor electrodes are in spiral wound form, and the spacer material is in the form of an open net or mesh.

25. The system of claim 1 wherein the capacitor electrodes are in crescent pleat form about a central tube, and the spacer material is in the form of an open net or mesh material.

26. The system of claim 1 wherein the capacitor electrodes are in flat, polygonal form, and the capacitor is placed within a flat, polygonal or circular box-shape cartridge.

27. The system of claim 1 whereby the capacitor electrodes are in the form of multiple rods or tubes.

28. The system of claim 1 whereby the capacitor electrodes are formed of a composite high surface area conductive material and include a conductive backing or fibrous network formed together as a single, integral material.

29. The system of claim 1 wherein the width spacing between the electrodes is between about 5 and 20 mils, and the length of the open flow path is less than about 12 inches.

30. The system of claim 1 wherein the spacer comprises biplanar netting material.

31. The system of claim 1 wherein the electrode includes a conductive backing layer.

32. The system of claim 1 wherein the internal electrical resistance of the capacitor is less than about four ohms.

33. The system of claim 1 wherein the electrodes comprise a non-conductive high surface area material in contact with a conductive backing material.

34. The system of claim 1 wherein the spacer is characterized by screen printed microprotrusions.

35. The system of claim 1 wherein the open flow path comprises straight multiple parallel flow paths of less than 50 mils and the lesser dimension of the X-Y-Z dimensions of the electrode.

\* \* \* \* \*